United States Patent [19]
Kura et al.

[11] Patent Number: 5,989,031
[45] Date of Patent: Nov. 23, 1999

[54] ARTIFICIAL TOOTH

[76] Inventors: Günter Kura, Römerstrasse 54, 50127 Bergheim; Frank Dietrich Braun, Ossum 14, 40668 Meerbusch; Harry Daug, In der Beek 71, 42113 Wuppertal, all of Germany

[21] Appl. No.: 08/776,744
[22] PCT Filed: Jul. 28, 1995
[86] PCT No.: PCT/EP95/03014
  § 371 Date: Apr. 15, 1997
  § 102(e) Date: Apr. 15, 1997
[87] PCT Pub. No.: WO96/03935
  PCT Pub. Date: Feb. 15, 1996

[30] Foreign Application Priority Data

Jul. 29, 1994 [DE] Germany ............... 44 26 994

[51] Int. Cl.⁶ ................................................ A61C 13/08
[52] U.S. Cl. .................................. 433/202.1; 433/203.1; 264/19
[58] Field of Search ...................... 433/202.1, 203.1, 433/212.1; 264/19, 20; 106/35

[56] References Cited

U.S. PATENT DOCUMENTS

| 2,514,076 | 7/1950 | Kelly | 264/20 |
| 4,134,935 | 1/1979 | Quiring et al. | 260/859 |
| 4,155,964 | 5/1979 | Aronow | 264/13 |
| 4,265,669 | 5/1981 | Starling et al. | 106/35 |
| 4,433,959 | 2/1984 | Faunce | 433/201 |
| 4,645,455 | 2/1987 | Kosmos | 433/203.1 |
| 5,151,044 | 9/1992 | Rotsaert | 433/202.1 |

FOREIGN PATENT DOCUMENTS 36 44 498 A1  7/1988  Germany.
38 27 657 A1  2/1990  Germany.

*Primary Examiner*—John J. Wilson
*Attorney, Agent, or Firm*—Jones & Askew

[57] ABSTRACT

An artificial tooth of plastic or ceramic material. The artificial tooth has a tooth body comprising an internal solid core (1) and at least one external layer (2) formed by injection molding and enveloping the solid core (1) at least in part.

23 Claims, 4 Drawing Sheets

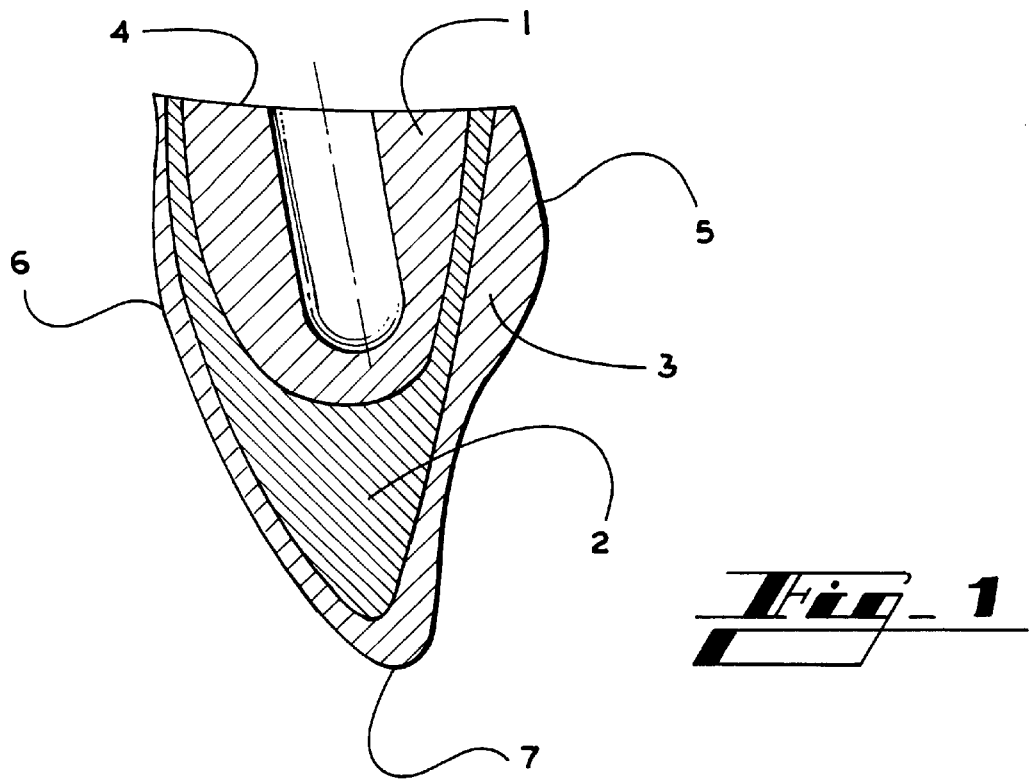
Fig_1
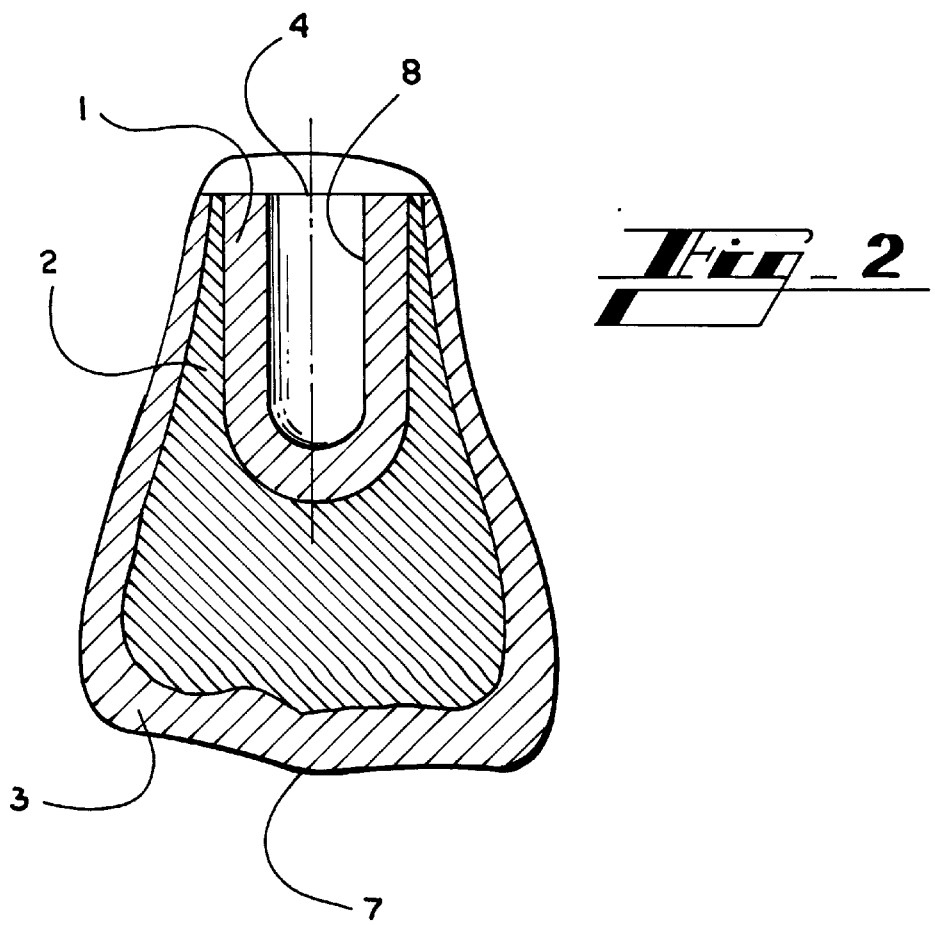
Fig_2

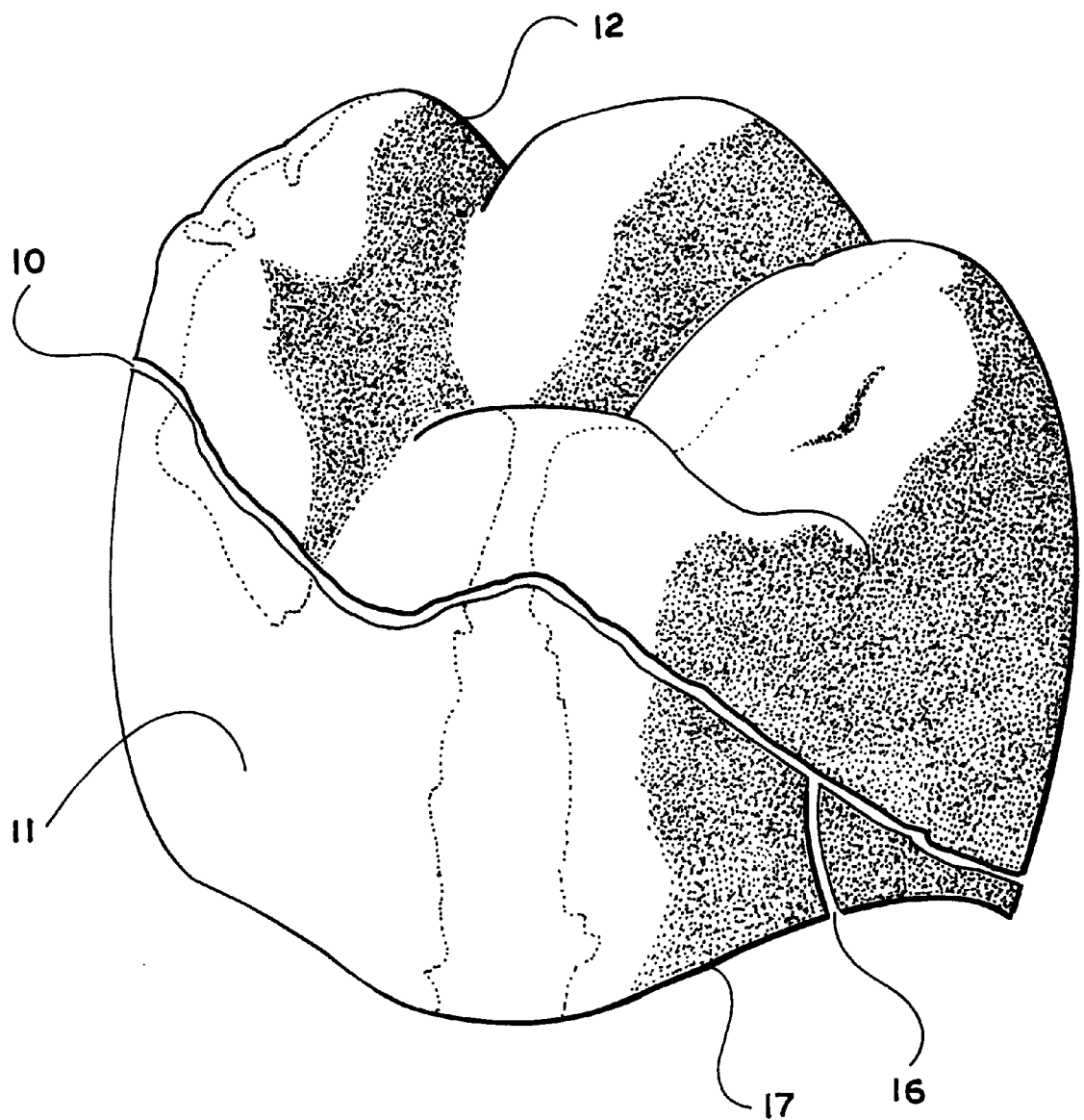
Fig_3

ARTIFICIAL TOOTH

FIELD OF THE INVENTION

The present invention pertains to an artificial tooth of plastic or ceramic material consisting of several layers and used in dental prosthetics.

BACKGROUND OF THE INVENTION

According to DIN 13914, artificial teeth for producing dental prostheses must consist of several layers because of the desired similarity to natural teeth. Such multilayer teeth have previously been produced exclusively by a pressing process, wherein the differently dyed pressing masses are placed by hand in the pressing tool. The pressing of the teeth is very labor-intensive. The distribution of the layers put in place by hand is subject to irregularities. The excess amounts necessary for pressing lead to considerable burr formation at the separating plane of the mold halves. This makes subsequent processing necessary. Thus considerable production effort is connected to the production of conventional multilevel teeth, so that these teeth are relatively expensive.

The present invention is based on the problem of creating an artificial tooth constructed of several layers whose production can be largely automated and in which a reproducible arrangement of layers is guaranteed and, in particular, burr formation is also minimized, so that low production costs result.

SUMMARY OF THE INVENTION

This problem is solved according to the invention in that a tooth body consists of an internal solid core and least one first injection-molded outer layer enveloping the solid core at least in part. It is advantageous in this regard according to the invention if the solid core is also formed by injection molding.

The invention relies upon the recognition that a considerable savings in cost can be achieved by injection molding technology, since injection molding is done completely automatically and hence a reproducible arrangement of layers can be guaranteed. This may involve a multicomponent injection molding process, wherein the material components form layers inside the tooth body so that, by dying the individual material components differently the natural tooth appearance can be optimally approximated.

In particular, one or more material layers, built up on the base of the injection-molded solid core, can be extruded onto it and envelop it. The tooth structure according to the invention in this case is such that the basal tooth side of the solid core is not enveloped, whereas the other sides of the tooth are formed by the material layers enveloping the solid core.

The present invention also pertains to a process for producing layered teeth by a multicomponent injection molding process. In this case, the entire injection cycle runs completely automatically, with the same arrangement of the layers in each cycle due to the nature of the process. Burr formation in injection molding is considerably less by comparison to the pressing process.

The solid core and the layers enveloping it can consist according to the invention of a plastic material made of a transparent (amorphous) plastic. In particular, an impact-resistant modified polymethylmethacrylate (PMMA) is used for this purpose. It can also be advantageous according to the invention if a plastic material consisting of a mixture of plastics with the same refraction index is used.

Alternatively, it is possible according to the invention to use as material a ceramic material consisting of an injection-moldable ceramic mass consisting of a ceramic powder with a plastic material additive serving as a binder.

BRIEF DESCRIPTION OF THE DRAWINGS

The invention will be discussed in greater detail on the basis of the embodiments show in the attached drawings. These show in FIG. 1 a section in the sagittal plane through an artificial tooth constructed according to the invention as a front tooth;

FIG. 2 a section in the frontal plane through the tooth of FIG. 1;

FIGS. 3 & 4 perspective views of a side tooth according to the invention; and

DETAILED DESCRIPTION OF PREFERRED EMBODIMENT

Figure 4:
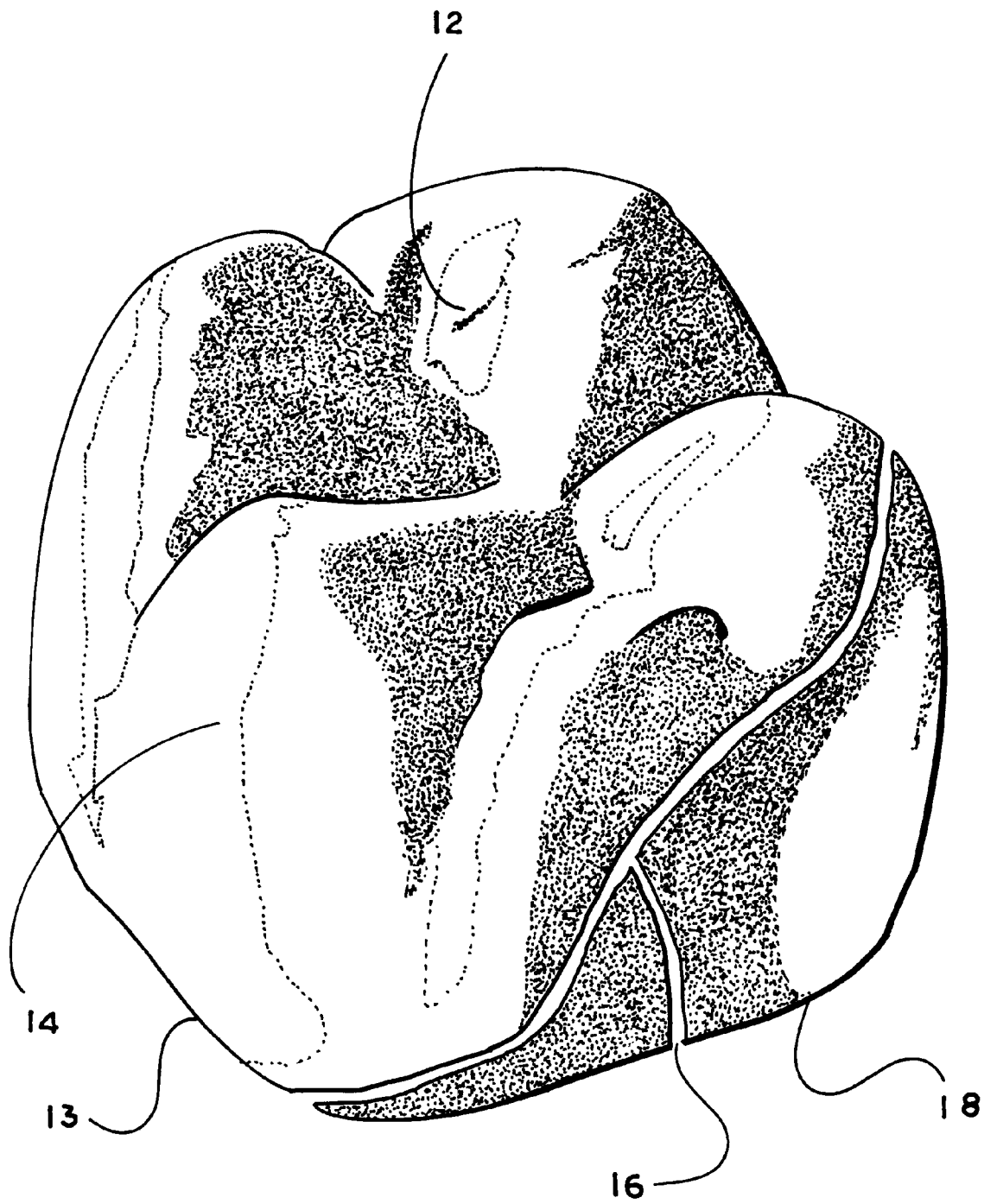

In the figures, identical features of the artificial tooth according to the invention are labeled with the same reference numerals.

As is seen from FIGS. 1 and 2, a tooth according to the invention consists of a tooth body with a solid core 1. The solid core 1 forms the basic element of the tooth, on which the additional external layers 2 and 3 are built up. In this respect, the basal side 4 of the solid core 1 remains bare, whereas the palatal side 5, the labial side 6 and the incisal side 7 of the tooth are formed by the external layers 2,3. The solid core 1 is constructed roughly in the shape of a truncated cone, with the side opposite the basal side 4 being rounded off. The external layer 2 directly enveloping the solid core 1 is formed with a small thickness in the area of the edge of the basal side 4, the tooth base, shaped with a small thickness, which amounts to 0.2 mm, for example. In the direction towards the incisal side 7 of the tooth, however, the external layer 2 increases considerably in thickness and is also shaped such that, together with the solid core 1, it practically forms the basic structure of the tooth. The outermost external layer 3 has essentially the same thickness around the periphery, with the palatal side 5 additionally modeled by the external layer 3, as shown, while the external layer 3 has roughly a constant thickness in the area of the labial side 6, as do the other areas, as shown in FIG. 2. A blind hole 8, adapted in size to the size of the respective tooth and whose diameter and depth may be roughly 2–3 mm and roughly 4–6 mm respectively, is formed in the basal side 4 of the solid core 1 in the tooth axis. The blind hole 8 is formed with smooth walls so that no sharp edges are present and therefore tension cracks cannot form. This blind hole 8 serves, on the one hand, for mounting the solid core 1 inside an injection form for conducting the injection-molding process and, on the other hand, for fastening the finished tooth on a plastic base when producing a dental prosthesis. A transparent (amorphous) plastic that meets the requirements of DIN 13931 or ISO 3336 can be used as the material for manufacturing the tooth according to the invention. Specifically, a transparent thermoplastic can be used. A suitable plastic material is polymethylmethacrylate (PMMA) and/or its copolymers. It is advantageous to use an impact-resistant modified PMMA. It may also be practical according to the invention if mixtures of plastics with an identical refraction index are employed. Such mixtures consist of a standard PMMA and impact-resistant modified PMMA, with a mixing ratio of 30% standard PMMA and 70% impact-resistant modified PMMA being practical. It is also possible, however, to employ a mixture of polymethyacrylmethylimide (PMMI) and a methylmethacrylate-styrene copolymer, where it is practical if 60% PMMI and 40% methylmethacrylate-styrene copolymer are present. It is also possible according to the invention for a mixture of a copolymer of methylmethacrylate and styrene with a methylmethacrylate content of more than 60% to be used.

It can also be advantageous according to the invention if an injection-moldable ceramic mass consisting of a ceramic powder such as $Al_2O_3$ or $ZrO_2$ with a plastic additive serving as a binder is used as the production material.

This injection-moldable ceramic mass is processed in an injection molding machine and the injection-molded tooth is removed as a so-called green product from the injection molding machine. The binder is removed from this green product in a binder-removal oven, that is, the plastic additive used as a binder is driven out, so that the binder is removed as completely as possible from the casting, with any change in shape being avoided if at all possible. Subsequently, there is a sintering process in a sintering oven and any required finishing work.

According to the invention, the solid core 1 and the external layers have different colorations. Thus the solid core 1 is advantageously colored dark, the translucent external layer 2 has a somewhat lighter coloration, and the outermost external layer 3 is light and translucent. It can also be practical to provide even more translucent external layers. Due to the enveloping construction of the layers 2,3 a color appearance optimally matched to natural teeth can be achieved. This of course makes color transitions without separation lines possible. Due to the formation of the blind holes 8 in the teeth according to the invention, a subsequent boring of anchoring holes is unnecessary, so that the risk of creating crack-generating sharp edges is excluded.

Specifically, a multicomponent injection molding process is employed for producing the tooth according to the invention. In case a three-layer tooth is being produced, i.e., a tooth according to FIGS. 1 and 2, the core material of the solid core 1 is a first step into a first tool cavity. After that, the tool opens and the tool half with the injection-molded solid core 1 turns by 120°. Here a plastic material of the type used has a plastic but already form-stable consistency and has been cooled down roughly to its glass transition temperature. Upon closure of the tool, the solid core 1 moves into a second, somewhat larger cavity for injecting the external layer 2. A temperature is present here at the interface between the core and the external layer 2 that permits a fusion of the two layers. After the injection of the external layer 2 around the core, the tool opens and the movable tool half turns by an additional 120°, so the injection-coated solid core 1 moves into a third cavity when the tool closes. In this cavity, which corresponds to the geometry of the finished tooth, the outer layer 3 is injected on the tooth. After sufficient cooling, the tool opens and the finished tooth is ejected. The temperature conditions while injecting the external layer 3 onto the external layer 2 are the same as those in injecting the plastic layer 2 onto the solid core 1. After the finished tooth has been ejected, the movable tool half turns by an additional 120° so that the tool is back in its initial position. The entire injection cycle runs completely automatically and the layers of the tooth according to the invention which are produced are the same in each cycle due to the process. The layers 1,2,3 preferably consist of the same plastic material, with these materials advantageously being colored differently. The injection of the respective successive layer is done so quickly that the contact temperature arising at the contact surface with the lower layer is higher than the softening temperature of the respective plastic.

An injection molding tool used according to the invention can be constructed such that several teeth, for instance a complete set of teeth, are injection-molded at one time.

Figure 5:
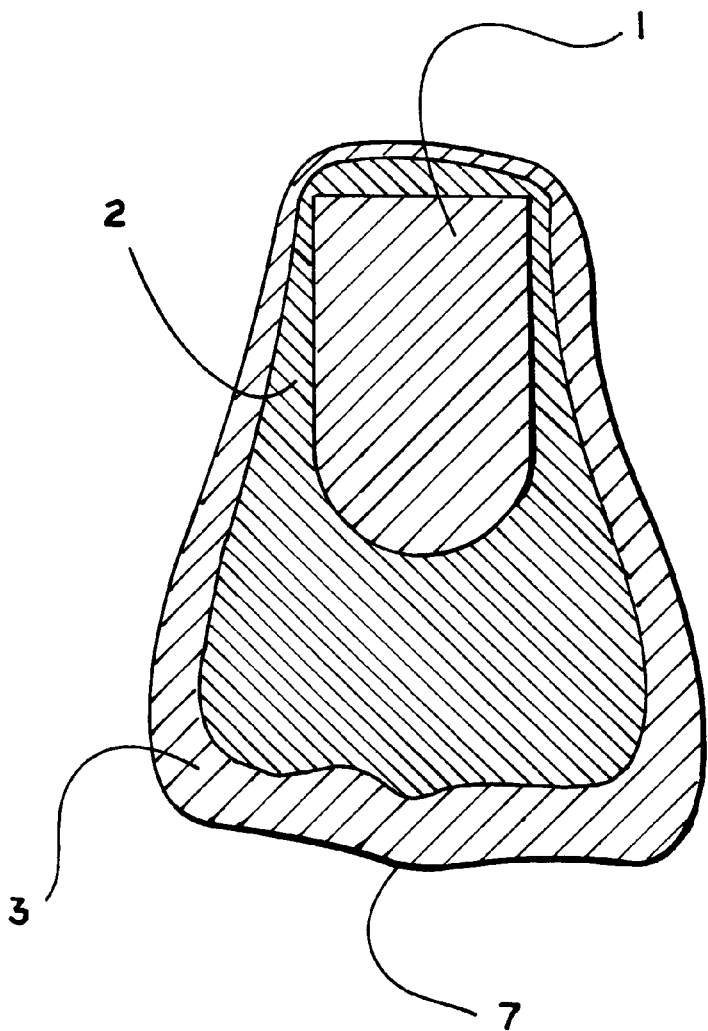
FIG. 5 an additional embodiment of a tooth according to the invention in the view of FIG. 2.

As an alternative production process to that according to the invention, it is also possible to use a multicomponent injection molding process in which an appropriately stratified structure of the tooth body is achieved solely by the metering of the differently colored materials, so that only the cavity with the tooth geometry is needed. In this case, using, for example three plastification units, the components for the outermost external layer 3 and the components for the external layer 2 are metered in succession into a feeder channel of the injection mold and then, after switching over to the third plastification unit with the succeeding component for the solid core 1, all three are injected into the tool in such a manner that the mold filling takes place in expansion flux. During advancement of the melt front a part of the front material adheres to the cold mold walls and thus forms the external layer 3. The metering is to be selected such that material of this component remains in the flow front until the complete filling of the mold. Due to a temperature gradient perpendicular to the mold wall, the succeeding component behaves similarly to the first, forms the middle external layer 2 and encloses the core material 1. In case of injection from the basal side, one obtains a layer structure similar to the illustration in FIGS. 1 and 2, however, with the solid core 1 also enclosed on the basal side by the external layers 2 and 3, see FIG. 5. Due to the nature of the process, the thickness of the external layers 2 and 3 increases slightly from the basal side towards the cutting edge, which improves the appearance of the tooth. The thickness of the external layers 2 and 3 can be influenced by the choice of process parameters, such as metered amount, mass temperature, tool temperature and injection rate. The injectable ceramic mass behaves in processing on the injection molding machine in a manner corresponding to a filled plastic, so that the advantageous processes as described above can also be applied even using the injection-moldable ceramic mass.

A side tooth produced according to the invention has in principle the same succession of layers as the front tooth according to FIGS. 1 and 2, with different fundamental structures of the solid core 1 and the external layers 2 and 3, due to the form of the side tooth. In this case the occlusal side 7 takes the place of the incisal side 7 and the buccal side 6 takes the place of the labial side 6.

It is shown in FIGS. 3 and 4 the course of the mold mark, created during removal of the finished injection-molded tooth body from the injection mold because of the position of its separation planes, in a side tooth according to the invention. It is provided according to the invention that the mold marks run on the finished tooth body such that they are not visible in the human mouth in the inserted state. In the tooth body of a side tooth according to the invention shown from a lingual perspective in FIG. 3, it is recognizable that a lingual mold mark 10 runs in the transition between the lingual side 11 and the occlusal surface 12 of the tooth body. In FIG. 4, which shows a buccal side view of a side tooth according to the invention, it is recognizable that a buccal mold mark 13 is provided in the transition between the buccal side 14 and the base 15 of the tooth body. It is also evident from FIGS. 3 and 4 that the mold marks 16 on the two side faces 17,18 of the tooth body each runs roughly diagonally connecting the ends of the lingual mold mark 10 and the buccal mold mark 13.

In a tooth element according to the invention formed as a front tooth, the mold marks are centrally arranged on the two side surfaces of the tooth body such that they run from the base of the tooth body to the tooth's cutting edge.

We claim:

1. Artificial tooth of plastic or ceramic material to replace a natural tooth, characterized by a tooth body comprising:
    an internal solid core (1) having plural sides, and at least one external thermoplastic layer (2) formed by injection molding and enveloping the solid core (1) at least in part;
    the solid core (1) being formed by injection molding;
    at least one additional external layer (3) applied on the first external layer (2) by injection molding;
    the molded external layers (2,3) being formed on a base formed by the solid core (1) as coating layers; and wherein
    the external layers (2,3) envelop the solid core (1) on all said sides.

2. Artificial tooth according to claim 1, characterized in that a plastic material made of a transparent (amorphous) plastic is used as production material.

3. Artificial tooth according to claim 2, characterized in that an impact-resistant modified polymethylmethacrylate (PMMA) is used as plastic material.

4. Artificial tooth according to claim 2, characterized in that a mixture of plastics with the same refractive index is used as plastic material.

5. Artificial tooth according to claim 2, characterized in that a mixture of copolymers consisting of methylmethacrylate (MMA) and styrene with an MMA content of more than 60% is used as plastic material.

6. Artificial tooth according to claim 1, characterized in that a ceramic material consisting of an injection-moldable ceramic mass of ceramic powder with a plastic material additive serving as binder, is used as production material.

7. Artificial tooth according to claim 1, characterized in that the artificial tooth is formed as a front tooth, and the solid core (1) is enveloped on the palatal (5), the labial (6) and the incisal (7) sides and in their connection regions by the external layers (2,3).

8. Artificial tooth according to claim 7, characterized in that the thickness of the external layer (2) immediately adjacent to the solid core (1) is thinnest in the area of the basal side (4), i.e., the tooth neck, and increases in the direction towards the occlusal and incisal sides (7), respectively, so that the solid core (1) and the external layer (2) jointly form the basic tooth structure.

9. Artificial tooth according to claim 1, characterized in that the artificial tooth is formed as a side tooth, and the solid core (1) is enveloped on the palatal (5), the buccal (6) and the occlusal (7) sides and in their connection regions by the external layers (2,3).

10. Artificial tooth according to claim 9, characterized in that the thickness of the external layer (2) immediately adjacent to the solid core (1) is thinnest in the area of the basal side (4), i.e., the tooth neck, and increases in the direction towards the occlusal and incisal sides (7), respectively, so that the solid core (1) and the external layer (2) jointly form the basic tooth structure.

11. Artificial tooth according to claim 1, characterized in that the outermost external layer (3) is modeled in the entire area of the tooth such that a flush-fitting tooth contour is produced thereby.

12. Artificial tooth according to claim 1, characterized in that in the basal side (4) of the solid core (1) a blind hole (8), whose diameter is roughly 2–3 mm and whose depth is roughly 4–6 mm, is bored in the direction of the tooth axis.

13. Artificial tooth according to claim 12, characterized in that the blind hole (8) has smooth walls.

14. Artificial tooth according to claim 1, characterized in that the solid core (1) and the external layers (2,3) are colored differently, the solid core (1) being dark, the first external layer (2) translucent and lighter, and the second external layer (3) colorless and translucent.

15. Artificial tooth according to claim 1, characterized in that the mold marks (10,13,16) formed by the injection molding tool on the finished injection-molded tooth body run such that they are not visible in the human mouth in the inserted state of the tooth body.

16. Artificial tooth according to claim 15, characterized in that, in a tooth body formed as a side tooth, a lingual mold mark (10) runs in the transition between the lingual side (11) and the occlusal surface (12) of the tooth body and a buccal mold mark (13) runs in the transition between the buccal side (14) and the base (15) of the tooth body.

17. Artificial tooth according to claim 15, characterized in that, in a tooth element formed as a front tooth, one mold mark (16) runs centrally on each of the side surfaces (17,18) of the tooth body from the base of the tooth body to the tooth's cutting edge.

18. Artificial tooth according to claim 17, characterized in that the mold marks (16) on the two side faces (17,18) of the tooth body each run roughly diagonally connecting the ends of the lingual mold mark (10) and the buccal mold mark (13).

19. Process for producing a tooth, of plastic or ceramic material, having a tooth body comprising an internal solid core (1) and at least one external layer (2) formed by injection molding and enveloping the solid core (1) at least in part, comprising the steps of:
    building the solid core (1) and the external layers (2,3) in a multicomponent by injection molding in succession on the core (1) and enveloping the core (1).

20. Process according to claim 19, characterized in that the injection of the respective succeeding layers is done sufficiently fast that temperature resulting on the contact surface with the lower layer is higher than the softening temperature of the plastic used.

21. Process according to claim 19, characterized in that upon opening of the injection molding tool the plastic material is still plastic but has a stable shape and preferably has roughly the glass temperature.

22. Process for producing an artificial tooth comprising an internal solid core (1) and at least one external thermoplastic layer (2) formed by injection molding and enveloping the solid core (1) at least in part, the solid core (1) being formed by injection molding, at least one additional external layer (3) applied on the first external layer (2) by injection molding, the molded external layers (2,3) being formed on a base formed by the solid core 91) as coating layers, and the external layers (2,3) enveloping the solid core (1) on all sides, characterized by producing the tooth body in a single injection process by controlled, metered injection of several thermoplastic components such that the tooth body builds up from the outside to the inside.

23. Process according to claim 22, characterized in that multiple teeth, are injection-molded by means of one injection molding tool.

\* \* \* \* \*